(12) United States Patent
Schmidt et al.

(10) Patent No.: US 10,836,644 B1
(45) Date of Patent: Nov. 17, 2020

(54) SMALL CRYSTAL SSZ-27, ITS SYNTHESIS AND USE

(71) Applicant: CHEVRON U.S.A. INC., San Ramon, CA (US)

(72) Inventors: Joel E. Schmidt, Oakland, CA (US); Stacey Ian Zones, San Francisco, CA (US)

(73) Assignee: CHEVRON U.S.A. INC., San Ramon, CA (US)

(*) Notice: Subject to any disclaimer, the term of this patent is extended or adjusted under 35 U.S.C. 154(b) by 0 days.

(21) Appl. No.: 16/994,788

(22) Filed: Aug. 17, 2020

Related U.S. Application Data

(60) Provisional application No. 62/909,609, filed on Oct. 2, 2019.

(51) Int. Cl.

| | |
|---|---|
| *C01B 39/48* | (2006.01) |
| *B01J 29/70* | (2006.01) |
| *C01B 39/02* | (2006.01) |
| *B01J 20/18* | (2006.01) |
| *B01J 20/30* | (2006.01) |
| *B01J 37/04* | (2006.01) |
| *B01J 37/00* | (2006.01) |
| *B01J 37/10* | (2006.01) |
| *B01D 53/94* | (2006.01) |

(52) U.S. Cl.
CPC .......... *C01B 39/48* (2013.01); *B01D 53/9418* (2013.01); *B01J 20/186* (2013.01); *B01J 20/3057* (2013.01); *B01J 20/3085* (2013.01); *B01J 29/70* (2013.01); *B01J 37/0018* (2013.01); *B01J 37/04* (2013.01); *B01J 37/10* (2013.01); *C01B 39/026* (2013.01); *B01D 2255/50* (2013.01); *C01P 2002/60* (2013.01); *C01P 2002/72* (2013.01); *C01P 2004/03* (2013.01); *C07C 2529/70* (2013.01)

(58) Field of Classification Search
CPC ... C01B 39/48; C01B 39/026; C01P 2002/60; C01P 2002/72; B01J 20/18; B01J 29/70; B01D 53/9418; B01D 2255/50; C07C 2529/70
See application file for complete search history.

(56) References Cited

U.S. PATENT DOCUMENTS

| | | | |
|---|---|---|---|
| 4,910,006 | A | 3/1990 | Zones et al. |
| 9,505,627 | B1 | 11/2016 | Zones et al. |
| 9,586,829 | B2 | 3/2017 | Zones et al. |
| 9,586,830 | B2 | 3/2017 | Zones et al. |

OTHER PUBLICATIONS

Kang et al., "Further Studies on How the Nature of Zeolite Cavities That are Bounded by Small Pores Influences the Conversion of Methanol to Light Olefins", ChemPhysChem 2018, 19, 412-419 (Year: 2018).*

Kang et al., "Further Studies on How the Nature of Zeolite Cavities That are Bounded by Small Pores Influences the Conversion of Methanol to Light Olefins", ChemPhysChem 2018, Supporting Information pp. 1-34 (Year: 2018).*

(Continued)

*Primary Examiner* — David M Brunsman

(57) ABSTRACT

The disclosure is related to small crystal forms of SSZ-27 molecular sieve materials, methods for making, and uses of the same.

12 Claims, 2 Drawing Sheets

(56) References Cited

OTHER PUBLICATIONS

S.I. Zones, M.M. Olmstead and D.S. Santilli "Guest/Host Relationships in the Synthesis of Large Pore Zeolite SSZ-26 from a Propellane Quaternary Ammonium Compound" J. Am. Chem. Soc. 1992, 114, 4195-4201.
S. Smeets, S.I. Zones, D. Xie, L. Palatinus, J. Pascual, S-J. Hwang, J.E. Schmidt and L.B. Mccusker "SSZ-27: A Small-Pore Zeolite with Large Heart-Shaped Cavities Determined by using Multi-crystal Electron Diffraction" Angew. Chem. Int. Ed. 2019, 58, 13080-13086. Supporting Information Included.

* cited by examiner

US 10,836,644 B1

SMALL CRYSTAL SSZ-27, ITS SYNTHESIS AND USE

CROSS-REFERENCE TO RELATED APPLICATIONS

This application claims priority to and the benefit of U.S. Provisional Application Ser. No. 62/909,609, filed Oct. 2, 2019.

FIELD

This disclosure relates to molecular sieve materials designated as SSZ-27, methods of making such materials, and uses of these materials.

BACKGROUND

The composition and characterizing X-ray diffraction pattern of molecular sieve SSZ-27 are disclosed in U.S. Pat. No. 9,586,829, which also describes the synthesis of the molecular sieve using one of the isomers of the structure directing agent (SDA) that is known to produce molecular sieve SSZ-26, a material containing both large- and medium-sized pores.

The framework structure of SSZ-27 can be described as a combination of two types of cavities, one of which is heart-shaped. The cavities are connected through shared 8-ring windows to create straight channels that are linked together in pairs to form a one-dimensional channel system. The heart-shaped cavity consists of 50 T-atoms ($[8^2 6^{10} 5^{10} 4^6]$) and has two 8-ring windows with free dimensions of about 3.6×5.5 Å, which are shared with a smaller cavity of 42 T-atoms ($[8^4 6^8 4^6]$). Each 42T cavity connects four heart-shaped cavities together. The heart-shaped cavities can be viewed as large side pockets which means that, despite being a small-pore zeolite, the internal volume of SSZ-27 is relatively large.

Conventional crystallization of an SSZ-27 reaction mixture produces large crystals in the 1 to 5 µm size range. Such large crystals inherently have slower diffusion. For separations and chemical reactions where diffusivity is critical, having a smaller crystal size provides a shorter diffusion path and therefore, enhances the mass transfer, improving the desired reaction pathways with a positive impact on the selectivity and conversion of such reactions.

According to the present disclosure, it has been found that small crystal forms of SSZ-27 can be produced by interzeolite conversion (i.e., the transformation of one zeolite structure into another zeolite structure) using syn,syn-N,N,N,N',N',N'-hexamethyl[4.3.3.0]propellane-8,11-diammonium cations.

SUMMARY

In a first aspect, there is provided a molecular sieve of SSZ-27 framework structure having a mean crystal size of no more than 500 nm.

In a second aspect, there is provided a molecular sieve of SSZ-27 framework structure having a mean crystal size of no more than 500 nm which comprises syn,syn-N,N,N,N',N',N'-hexamethyl[4.3.3.0]propellane-8,11-diammonium cations in its pores.

In a third aspect, there is provided a method of synthesizing a molecular sieve of SSZ-27 framework structure having a mean crystal size of no more than 500 nm, the method comprising: (a) providing a reaction mixture comprising: (1) a FAU framework type zeolite; (2) a source of a Group 1 or Group 2 metal (M); (3) a structure directing agent comprising syn,syn-N,N,N,N',N',N'-hexamethyl[4.3.3.0]propellane-8,11-diammonium cations (Q); (4) a source of hydroxide ions; and (5) water; and (b) subjecting the reaction mixture to crystallization conditions sufficient to form crystals of a molecular sieve of SSZ-27 framework structure.

In a fourth aspect, there is provided a process for separating at least two components, the process comprising contacting the at least two components with a molecular sieve of SSZ-27 framework structure having a mean crystal size of no more than 500 nm to generate at least one separated component.

In a fifth aspect, there is provided a process for converting a feedstock comprising an organic compound to a conversion product which comprises contacting the feedstock at organic compound conversion conditions with a catalyst comprising a molecular sieve of SSZ-27 framework structure having a mean crystal size of no more than 500 nm.

In a sixth aspect, there is provided process for treating an exhaust gas comprising contacting a combustion exhaust gas containing nitrogen oxides ($NO_x$) and/or $NH_3$ with a catalyst comprising a molecular sieve of SSZ-27 framework structure having a mean crystal size of no more than 500 nm to selectively reduce at least a portion of the $NO_x$ into $N_2$ and $H_2O$ and/or oxidize at least a portion of the $NH_3$.

DETAILED DESCRIPTION

Definitions

Figure 1A:
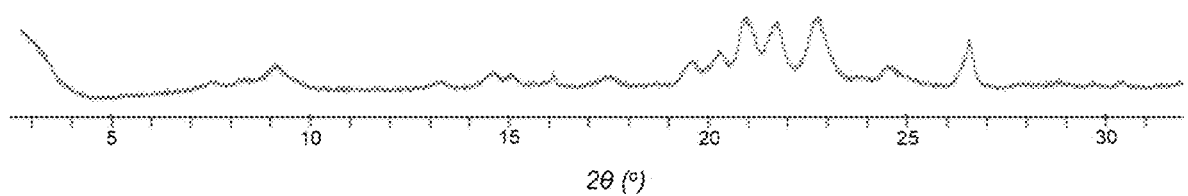
FIG. 1(a) shows a powder X-ray diffraction (XRD) pattern of the as-synthesized SSZ-27 product of Example 2.

The term "framework type" as used herein has the meaning described in the "*Atlas of Zeoite Framework Types*," by Ch. Baerlocher, L. B. McCusker and D. H. Olson (Elsevier, Sixth Revised Edition, 2007).

The term "as-synthesized" is employed herein to refer to a molecular sieve in its form after crystallization, prior to removal of the structure directing agent.

The term "anhydrous" is employed herein to refer to a molecular sieve substantially devoid of both physically adsorbed and chemically adsorbed water.

As used herein, the numbering scheme for the Periodic Table Groups is as disclosed in *Chem. Eng. News* 1985, 63(5), 26-27.

Synthesis of the Molecular Sieve

Small crystal forms of molecular sieve SSZ-27 can be synthesized by: (a) providing a reaction mixture comprising: (1) a FAU framework type zeolite; (2) a source of a Group 1 or Group 2 metal (M); (3) a structure directing agent comprising syn,syn-N,N,N,N',N',N'-hexamethyl[4.3.3.0] propellane-8,11-diammonium cations (Q); (4) a source of hydroxide ions; and (5) water; and (b) subjecting the reaction mixture to crystallization conditions sufficient to from crystal of a molecular sieve of SSZ-27 framework structure.

The reaction mixture can have a composition, in terms of molar ratios, within the ranges set forth in Table 1:

TABLE 1

| Reactants | Broadest | Secondary |
|---|---|---|
| $SiO_2/Al_2O_3$ | 20 to 100 | 20 to 80 |
| $M/SiO_2$ | 0.05 to 0.50 | 0.15 to 0.30 |
| $Q/SiO_2$ | 0.10 to 0.40 | 0.10 to 0.30 |
| $OH/SiO_2$ | 0.25 to 0.60 | 0.25 to 0.50 |
| $H_2O/SiO_2$ | 10 to 60 | 20 to 50 | wherein M is a Group 1 or Group 2 metal; and Q comprises syn,syn-N,N,N,N',N',N'-hexamethyl[4.3.3.0]propellane-8,11-diammonium cations.

The FAU framework type zeolite can comprise two or more zeolites. The two or more zeolites can have different silica-to-alumina ratios. Different zeolites Y are examples of this. The FAU framework type zeolite can be used as the sole or predominant source of silicon and aluminum in the reaction mixture.

The Group 1 or Group 2 metal (M) can be any M-containing compound not detrimental to crystallization process can be used. The Group 1 or Group 2 metal may be sodium or potassium. Sources of the Group 1 or Group 2 metal can include metal hydroxide, metal oxide, metal halide, metal sulfate, metal nitrate, and metal carboxylate. As used here, the phrase "Group 1 or Group 2 metal" does not mean the Group 1 metals and Group 2 metals are used in the alternative, but instead that one or more Group 1 metals can be used alone or in combination with one or more Group 2 metals and that one or more Group 2 metals can be used alone or in combination with one or more Group 1 metals.

In preparing the present molecular sieve, the structure directing agent comprises syn,syn-N,N,N,N',N',N'-hexamethyl[4.3.3.0]propellane-8,11-diammonium cations (Q), represented by the following structure (1):

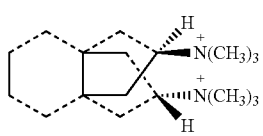

(1)

Suitable sources of Q are the hydroxides and/or other salts of the quaternary ammonium compound.

The reaction mixture may also contain seeds of a molecular sieve material, such as SSZ-27 from a previous synthesis, desirably in an amount of from 0.01 to 10,000 ppm by weight (e.g., from 100 to 5000 ppm by weight) of the reaction mixture. Seeding can be advantageous in decreasing the amount of time necessary for complete crystallization to occur. In addition, seeding can lead to an increased purity of the product obtained by promoting the nucleation and/or formation of SSZ-27 over any undesired phases.

It is noted that the reaction mixture components can be supplied by more than one source. Also, two or more reaction components can be provided by one source. The reaction mixture can be prepared either batchwise or continuously.

Crystallization of the desired molecular sieve from the above reaction mixture can be carried out under either static, tumbled or stirred conditions in a suitable reactor vessel, such as for example polypropylene jars or Teflon-lined or stainless-steel autoclaves, at a temperature of greater than 160° C. to 200° C. (e.g., 165° C. to 185° C.) for a time sufficient for crystallization to occur at the temperature used (e.g., from about 1 to 14 days). Crystallization temperatures of greater than 160° C. are desired in order to favor the formation of SSZ-27 over SSZ-26. Crystallization is usually carried out in an autoclave so that the reaction mixture is subject to autogenous pressure.

Once the desired molecular sieve crystals have formed, the solid product can be separated from the reaction mixture by standard mechanical separation techniques such as centrifugation or filtration. The recovered crystals are water-washed and then dried, for several seconds to a few minutes (e.g., 5 seconds to 10 minutes for flash drying) or several hours (e.g., 4 to 24 hours for oven drying at 75° C. to 150° C.), to obtain the as-synthesized molecular sieve crystals. The drying step can be performed at atmospheric pressure or under vacuum.

As a result of the crystallization process, the recovered crystalline molecular sieve product contains within its pores at least a portion of the structure directing agent used in its synthesis.

The as-synthesized molecular sieve may be subjected to subsequent treatment to remove part or all of the structure directing agent used in its synthesis. Removal of the structure directing agent may be carried out using thermal treatment (e.g., calcination) in which the as-synthesized material is heated in an atmosphere selected from air, nitrogen, or a mixture thereof at a temperature sufficient to remove part or all of the structure directing agent. The thermal treatment may be performed at a temperature of up to 700° C. (e.g., 400° C. to 700° C.) for at least a minute and generally not longer than 20 hours (e.g., from 1 to 12 hours, or from 3 to 8 hours). While sub-atmospheric pressure may be employed for the thermal treatment, atmospheric pressure is desired for reasons of convenience. Additionally or alternatively, the structure directing agent can be removed by treatment with ozone.

Any extra-framework Group 1 or Group 2 metal cations in the molecular sieve can be replaced in accordance with techniques well known in the art (e.g., by ion exchange) with hydrogen, ammonium, or any desired metal cation.

Characterization of the Molecular Sieve

In its as-synthesized and anhydrous form, the present SSZ-27 molecular sieve can have a chemical composition, in terms of molar ratios, within the ranges set forth in Table 2:

TABLE 2

| | Broadest | Secondary |
|---|---|---|
| $SiO_2/Al_2O_3$ | 20 to 80 | 20 to 35 |
| $Q/SiO_2$ | >0 to 0.1 | >0 to 0.1 |
| $M/SiO_2$ | >0 to 0.1 | >0 to 0.1 | wherein Q comprises syn,syn-N,N,N,N',N',N'-hexamethyl[4.3.3.0]propellane-8,11-diammonium cations; and M is a Group 1 or Group 2 metal.

The SSZ-27 crystals of the present disclosure preferably can each independently have a mean crystal size of no more than about 500 nm, no more than about 250 nm, or no more than about 150 nm. Additionally, or alternatively, the SSZ-27 crystals of the present disclosure can have a mean crystal size in a range of 25 to 500 nm (e.g., 25 to 250 nm, 25 to 125 nm, 50 to 500 nm, or 50 to 250 nm). Conventional SSZ-27, prepared according U.S. Pat. No. 9,586,830, generally has a mean crystal size of at least 1 μm (e.g., 1 to 5 μm).

The crystal size is based on individual crystals (including twinned crystals) but does not include agglomerations of crystals. Crystal size is the length of longest diagonal of the three-dimensional crystal. Direct measurement of the crystal size can be performed using microscopy methods, such as SEM and TEM. For example, measurement by SEM involves examining the morphology of materials at high magnifications (typically 1000× to 50,000×). The SEM method can be performed by distributing a representative portion of the molecular sieve powder on a suitable mount such that individual particles are reasonably evenly spread out across the field of view at 1000× to 50,000× magnification. From this population, a statistically significant sample of random individual crystals (e.g., 50-200) are examined and the longest diagonal of the individual crystals are measured and recorded. Particles that are clearly large polycrystalline aggregates should not be included the measurements. Based on these measurements, the arithmetic mean of the sample crystal sizes is calculated. Mean crystal size can also be determined by X-ray diffraction using the Scherrer equation.

As taught by U.S. Pat. No. 9,586,829, molecular sieve SSZ-27 has a powder X-ray diffraction pattern which, in its as-synthesized form, includes at least the peaks set forth in Table 3 below and which, in its calcined form, includes at least the peaks set forth in Table 4.

TABLE 3

Characteristic Peaks for As-Synthesized SSZ-27

| 2-Theta[a] | d-spacing, nm | Relative Intensity[b] |
|---|---|---|
| 7.57 | 1.167 | W |
| 8.62 | 1.025 | W |
| 9.35 | 0.946 | M |
| 9.83 | 0.900 | W |
| 13.55 | 0.653 | W |
| 14.80 | 0.598 | W |
| 15.27 | 0.580 | W |
| 16.25 | 0.545 | W |
| 17.72 | 0.500 | W |
| 19.76 | 0.449 | M |
| 20.50 | 0.433 | W |
| 21.08 | 0.421 | S |
| 21.30 | 0.417 | M |
| 21.93 | 0.405 | S |
| 22.95 | 0.387 | VS |

[a] ±0.20
[b] The powder XRD patterns provided herein are based on a relative intensity scale in which the strongest line in the XRD pattern is assigned a value of 100: W = weak (>0 to ≤20); M = medium (≥20 to ≤40); S = strong (>40 to ≤60); and VS = very strong (>60 to ≤100).

TABLE 4

Characteristic Peaks for Calcined SSZ-27

| 2-Theta[a] | d-spacing, nm | Relative Intensity |
|---|---|---|
| 7.50 | 1.177 | W |
| 8.65 | 1.021 | W |
| 9.47 | 0.933 | VS |
| 9.94 | 0.889 | M |
| 13.47 | 0.657 | M |
| 14.86 | 0.596 | M |
| 16.07 | 0.551 | W |
| 16.37 | 0.541 | W |
| 17.92 | 0.495 | W |
| 19.92 | 0.445 | W |
| 20.66 | 0.430 | W |
| 21.14 | 0.420 | W |
| 21.34 | 0.416 | W |
| 22.07 | 0.402 | M |
| 23.17 | 0.384 | M |

[a] ±0.20

Small crystal SSZ-27 prepared as described herein, in its as-synthesized or calcined form, can have a characteristic X-ray powder diffraction pattern substantially the same as shown in FIG. 1(a). It is known that certain lines in the powder X-ray diffraction patterns of zeolites can tend to broaden as the relevant dimension of the zeolite crystal decreases, so that adjacent lines may begin to overlap and thereby appear as only partially resolved peaks or as unresolved broad peaks.

The powder X-ray diffraction patterns presented herein were collected by standard techniques. The radiation was CuKα radiation. The peak heights and the positions, as a function of 2θ where θ is the Bragg angle, were read from the relative intensities of the peaks (adjusting for background), and d, the interplanar spacing corresponding to the recorded lines, can be calculated.

INDUSTRIAL APPLICABILITY

The present SSZ-27 molecular sieve can be used for separating mixtures of molecular species, removing contaminants through ion exchange and catalyzing various organic conversion processes. Separation of molecular species can be based either on the molecular size (kinetic diameter) or on the degree of polarity of the molecular species. The separation process may comprise contacting at least two components with the SSZ-27 molecular sieve to generate at least one separated component.

The present SSZ-27 molecular sieve may be appropriate for use as selective adsorbent of $CO_2$ in the presence of hydrocarbons (e.g., methane, ethane, ethylene, and combinations of the same) in streams that contain these gases, well as adsorbent in powdered or pelletized form or in membrane form. The SSZ-27 molecular sieve may be appropriate for the separation in adsorption processes of hydrocarbons of 1 or 2 carbon atoms that contain these gases, as well as adsorbent in powdered or pelletized form or in membrane form. For example, the SSZ-27 may be used as a selective adsorbent of ethylene in the presence of ethane. The SSZ-27 molecular sieve may also be used as selective adsorbent of ethylene in the presence of methane.

The present SSZ-27 molecular sieve can be used as a catalyst to catalyze a wide variety of organic compound conversion processes. Examples of organic conversion processes which may be catalyzed by the SSZ-27 molecular sieve described herein can include converting an oxygenate to an olefin, aminating a lower alcohol, and carbonylating dimethyl ether with CO at low temperatures. Methanol is a particularly preferred oxygenate for the synthesis of ethylene and/or propylene.

The present SSZ-27 molecular sieve or a metal containing SSZ-27 can promote the reaction of a reductant (e.g., $NH_3$) with nitrogen oxides ($NO_x$) to selectively form elemental nitrogen ($N_2$) and water ($H_2O$). Thus, the catalyst can be formulated to favor the reduction of nitrogen oxides with a reductant (i.e., an SCR catalyst). Examples of such reductants include hydrocarbons (e.g., $C_3$-$C_6$ hydrocarbons) and nitrogenous reductants such as ammonia and ammonia hydrazine or any suitable ammonia precursor, such as urea, ammonium carbonate, ammonium carbamate, ammonium hydrogen carbonate or ammonium formate.

The present SSZ-27 molecular sieve or a metal containing SSZ-27, can also promote the oxidation of ammonia. SSZ-27 can contain one or more metal ions, such as copper or iron, that are impregnated into molecular sieve. The catalyst can be formulated to favor the oxidation of ammonia with oxygen, particularly at concentrations of ammonia typically encountered downstream of an SCR catalyst (e.g., ammonia oxidation (AMOX) catalyst, such as an ammonia slip catalyst (ASC)).

EXAMPLES

The following illustrative examples are intended to be non-limiting.

Example 1

Synthesis of Structure Directing Agent

An isomeric mixture of N,N,N,N',N',N'-hexamethyl[4.3.3.0]propellane-8,11-diammonium diiodide was prepared as described in U.S. Pat. No. 4,910,006. The desired isomeric product, syn, syn-N,N,N,N',N',N'-hexamethyl[4.3.3.0]propellane-8,11-diammonium diiodide, was isolated by selective recrystallization from warmed acetonitrile and water (13/1 v/v) as described by S. Smeets et al. (*Angew. Chem. Int. Ed.* 2019, 58, 2-9) until the product was deemed pure by H NMR spectroscopy.

The diiodide salt was then dissolved in deionized water and stirred overnight with an excess of BIO-RAD AG® 1-X8 hydroxide ion-exchange resin. The resin was filtered, and the filtrate analyzed for hydroxide content by titration with dilute HCl.

Example 2

Synthesis of Small Crystal SSZ-27

A suspension was prepared by mixing 0.5 mmoles of a solution of syn, syn-N,N,N,N',N',N'-hexamethyl[4.3.3.0]propellane-8,11-diammonium dihydroxide (based upon hydroxide contribution) in 0.58 g of solution with 1 g of 1 N NaOH, 1 g of deionized water, and 0.36 g of CBV720 Y-zeolite powder (Zeolyst International; $SiO_2/Al_2O_3$ molar ratio=30) inside a Teflon liner for a 23-mL steel Parr autoclave. The liner was then capped, sealed inside the 23-mL autoclave, and heated at 170° C. under tumbling conditions (~43 rpm) inside a convection oven for 7-10 days. The solids were then isolated by centrifugation, washed with deionized water, and dried in an oven at 95° C.

The resulting as-synthesized product was analyzed by powder XRD and SEM.

Figure 1B:
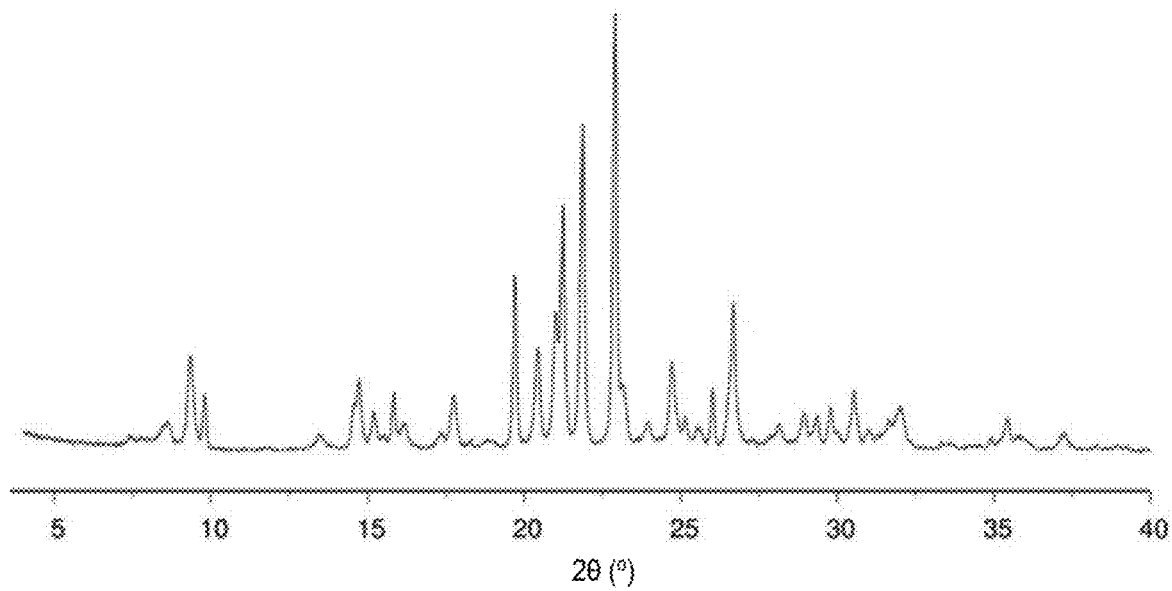
FIG. 1(b) shows a powder XRD pattern of conventional as-synthesized SSZ-27 prepared according to U.S. Pat. No. 9,586,829.

The powder XRD pattern of the product is shown in FIG. 1(a) and indicates that the product has significantly decreased crystal size as inferred from the peak broadening in the powder XRD pattern. For comparison, the powder XRD pattern of conventional as-synthesized SSZ-27, prepared according to U.S. Pat. No. 9,586,829, is shown in FIG. 1(b).

Figure 2A:
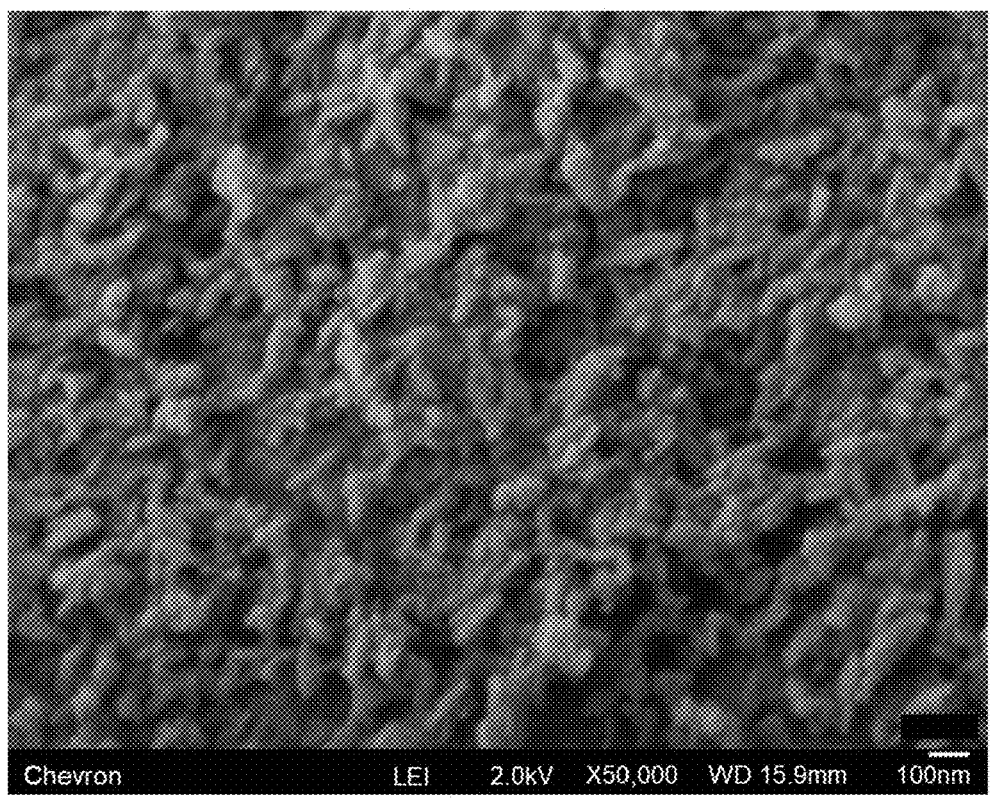
FIG. 2(a) shows a Scanning Electron Micrograph (SEM) image the as-synthesized SSZ-27 product of Example 2.
Figure 2B:
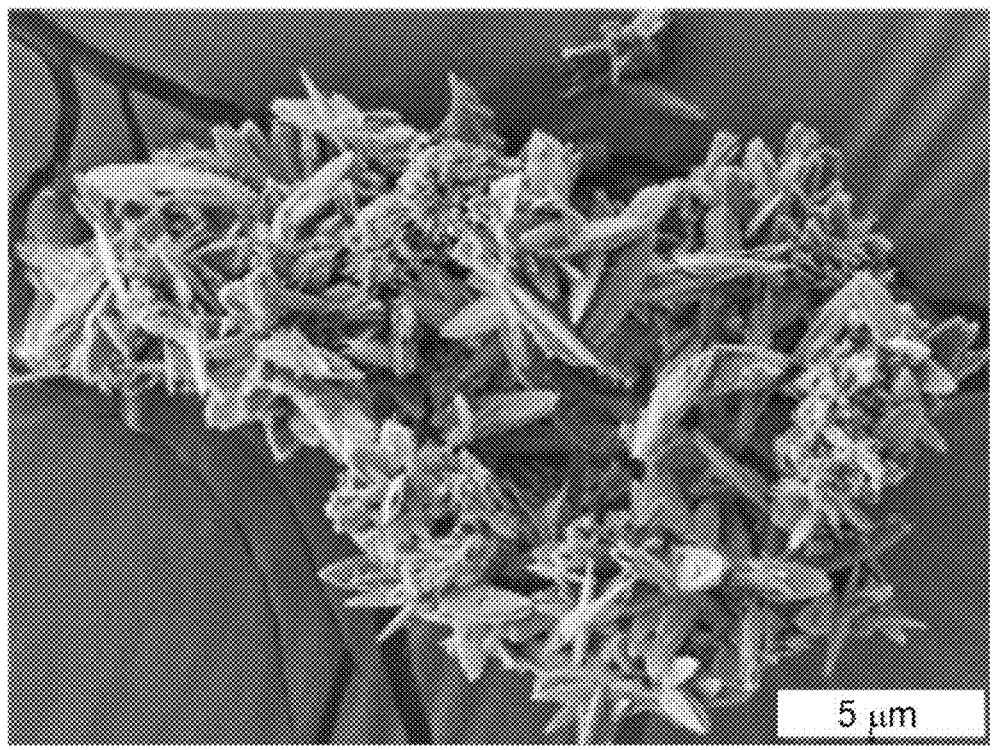
FIG. 2(b) shows a SEM image of conventional as-synthesized SSZ-27 prepared according to U.S. Pat. No. 9,586,829.

A SEM image of the product is provided in FIG. 2(a) and shows that the crystals are in the form of small primary crystallites having a crystal size of less 500 nm. For comparison, a SEM image of conventional as-synthesized SSZ-27, prepared according to U.S. Pat. No. 9,586,829, is provided in FIG. 2(b) and shows that the crystals have a crystal size of greater than 1 m.

As determined by Inductively Coupled Plasma (ICP) elemental analysis, the as-synthesized product had the following elemental composition: Si=34.0%; Al=2.27%; Na=0.266%.

The invention claimed is:

1. A molecular sieve of SSZ-27 framework structure comprising crystals having a mean crystal size of 500 nm or less.

2. The molecular sieve of claim 1, further comprising syn,syn-N,N,N,N',N',N'-hexamethyl[4.3.3.0]propellane-8,11-diammonium cations in its pores.

3. The molecular sieve of claim 1, having a molar ratio of $SiO_2/Al_2O_3$ in a range of 20 to 80.

4. The molecular sieve of claim 1, which exhibits a powder X-ray diffraction pattern substantially the same as shown in FIG. 1(a).

5. A method of synthesizing the molecular sieve of claim 1, the method comprising:
(a) providing a reaction mixture comprising:
(1) a zeolite of FAU framework type;
(2) a source of a Group 1 or Group 2 metal (M);
(3) a structure directing agent comprising syn,syn-N,N,N,N',N',N'-hexamethyl[4.3.3.0]propellane-8,11-diammonium cations (Q);
(4) a source of hydroxide ions; and
(5) water; and
(b) subjecting the reaction mixture to crystallization conditions sufficient to form crystals of a molecular sieve of SSZ-27 framework structure;
wherein the FAU framework type zeolite is the sole source of silica and aluminum in the reaction mixture.

6. The method of claim 5, wherein the reaction mixture has a composition, in terms of molar ratios, as follows:

| | |
|---|---|
| $SiO_2/Al_2O_3$ | 20 to 100 |
| $M/SiO_2$ | 0.05 to 0.50 |
| $Q/SiO_2$ | 0.10 to 0.40 |
| $OH/SiO_2$ | 0.25 to 0.60 |
| $H_2O/SiO_2$ | 10 to 60. |

7. The method of claim 5, wherein the reaction mixture has a composition, in terms of molar ratios, as follows:

| | |
|---|---|
| $SiO_2/Al_2O_3$ | 20 to 80 |
| $M/SiO_2$ | 0.15 to 0.30 |
| $Q/SiO_2$ | 0.10 to 0.30 |
| $OH/SiO_2$ | 0.25 to 0.50 |
| $H_2O/SiO_2$ | 20 to 50. |

8. The method of claim 5, wherein the FAU framework type zeolite is a Y zeolite.

9. The method of claim 5, wherein the crystallization conditions include a temperature in a range of greater than 160° C. to 200° C.

10. A process for separating at least two components, the process comprising contacting the at least two components with the molecular sieve of claim 1 to generate at least one separated component.

11. A process for converting a feedstock comprising an organic compound to a conversion product, the process comprising contacting the feedstock at organic compound conversion conditions with a catalyst comprising the molecular sieve of claim 1.

12. A process for treating an exhaust gas, the process comprising contacting a combustion exhaust gas containing nitrogen oxides ($NO_x$) and/or $NH_3$ with a catalyst comprising the molecular sieve of claim 1 to selectively reduce at least a portion of the $NO_x$ into $N_2$ and $H_2O$ and/or oxidize at least a portion of the $NH_3$.

\* \* \* \* \*